(12) United States Patent
Von Arx et al.

(10) Patent No.: US 6,574,510 B2
(45) Date of Patent: Jun. 3, 2003

(54) TELEMETRY APPARATUS AND METHOD FOR AN IMPLANTABLE MEDICAL DEVICE

(75) Inventors: Jeffrey A. Von Arx, Minneapolis, MN (US); Mark D. Amundson, Cambridge, MN (US); William R. Mass, Maple Grove, MN (US); Ron Balczewski, Roseville, MN (US); William J. Linder, Golden Valley, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 166 days.

(21) Appl. No.: 09/727,093

(22) Filed: Nov. 30, 2000

(65) Prior Publication Data

US 2002/0065539 A1 May 30, 2002

(51) Int. Cl.[7] .............................................. A61N 1/372
(52) U.S. Cl. ........................... 607/60; 607/32; 128/901; 340/572.7; 340/573.1
(58) Field of Search ................................. 128/901, 903; 340/539, 572.7, 573.1; 343/723, 750, 861, 895; 607/30, 31, 32, 60

(56) References Cited

U.S. PATENT DOCUMENTS

| 4,230,128 A | 10/1980 | Aramayo | 128/763 |
|---|---|---|---|
| 4,556,063 A | 12/1985 | Thompson et al. | 128/419 PT |
| 5,058,581 A | * 10/1991 | Silvian | 128/903 |
| 5,113,869 A | 5/1992 | Nappholz et al. | 128/696 |
| 5,127,404 A | 7/1992 | Wyborny et al. | 128/419 P |
| 5,314,453 A | 5/1994 | Jeutter | 607/61 |
| 5,337,756 A | 8/1994 | Barbier et al. | 128/763 |
| 5,342,408 A | 8/1994 | deCoriolis et al. | 607/32 |
| 5,354,319 A | * 10/1994 | Wyborny et al. | 128/903 |
| 5,562,713 A | 10/1996 | Silvian | 607/32 |
| 5,626,630 A | * 5/1997 | Markowitz et al. | 128/903 |
| 5,683,432 A | 11/1997 | Goedeke et al. | 607/32 |
| 5,735,887 A | 4/1998 | Barreras, Sr. et al. | 607/60 |
| 5,861,019 A | 1/1999 | Sun et al. | 607/60 |
| 5,862,803 A | 1/1999 | Besson et al. | 128/696 |
| 5,957,854 A | 9/1999 | Besson et al. | 600/509 |
| 6,009,350 A | 12/1999 | Renken | 607/32 |
| 6,115,636 A | 9/2000 | Ryan | 607/60 |
| 6,141,584 A | * 10/2000 | Rockwell et al. | 128/903 |
| 6,169,925 B1 | 1/2001 | Villaseca et al. | 607/60 |
| 6,434,429 B1 | * 8/2002 | Kraus et al. | 607/60 |

* cited by examiner

Primary Examiner—Michael Powell Buiz
Assistant Examiner—Ramesh Krishnamurthy
(74) Attorney, Agent, or Firm—Schwegman, Lundberg, Woessner & Kluth, P.A.

(57) ABSTRACT

An apparatus and method for enabling radio-frequency communications with an implantable medical device utilizing far-field electromagnetic radiation. Such radio-frequency communications can take place over much greater distances than with inductively coupled antennas.

30 Claims, 3 Drawing Sheets

TELEMETRY APPARATUS AND METHOD FOR AN IMPLANTABLE MEDICAL DEVICE

FIELD OF THE INVENTION

This invention pertains to implantable medical devices such as cardiac pacemakers and implantable cardioverter/defibrillators. In particular, the invention relates to an apparatus and method for enabling radio-frequency telemetry in such devices.

BACKGROUND

Implantable medical devices, including cardiac rhythm management devices such as pacemakers and implantable cardioverter/defibrillators, typically have the capability to communicate data with a device called an external programmer via a radio-frequency telemetry link. A clinician may use such an external programmer to program the operating parameters of an implanted medical device. For example, the pacing mode and other operating characteristics of a pacemaker are typically modified after implantation in this manner. Modern implantable devices also include the capability for bidirectional communication so that information can be transmitted to the programmer from the implanted device. Among the data which may typically be telemetered from an implantable device are various operating parameters and physiological data, the latter either collected in real-time or stored from previous monitoring operations.

Telemetry systems for implantable medical devices utilize radio-frequency energy to enable bidirectional communication between the implantable device and an external programmer. An exemplary telemetry system for an external programmer and a cardiac pacemaker is described in U.S. Pat. No. 4,562,841, issued to Brockway et al. and assigned to Cardiac Pacemakers, Inc., the disclosure of which is incorporated herein by reference. A radio-frequency carrier is modulated with digital information, typically by amplitude shift keying where the presence or absence of pulses in the signal constitute binary symbols or bits. The external programmer transmits and receives the radio signal with an antenna incorporated into a wand which can be positioned in proximity to the implanted device. The implantable device also generates and receives the radio signal by means of an antenna, typically formed by a wire coil wrapped around the periphery of the inside of the device casing.

In previous telemetry systems, the implantable device and the external programmer communicate by generating and sensing a modulated electromagnetic field in the near-field region with the antennas of the respective devices inductively coupled together. The wand must therefore be in close proximity to the implantable device, typically within a few inches, in order for communications to take place. This requirement is an inconvenience for a clinician and limits the situations in which telemetry can take place.

SUMMARY OF THE INVENTION

The present invention is an apparatus and method for enabling communications with an implantable medical device utilizing far-field electromagnetic radiation. Using far-field radiation allows communications over much greater distances than with inductively coupled antennas. In accordance with the invention, a conductor extending from the implantable device acts as an antenna that radiates and receives far-field radio-frequency radiation modulated with telemetry data. The antenna is dimensioned such that a substantial portion of the radio-frequency energy delivered to it at a specified frequency by a transmitter in the implantable device is emitted as far-field electromagnetic radiation. A tuning circuit may be used to tune the antenna by optimizing its impedance. In one embodiment, a therapy lead of a cardiac rhythm management device which is otherwise used for stimulating and/or sensing electrical activity in the heart has incorporated therein a wire antenna. Specialized structures may also be incorporated into such a therapy lead in order to isolate a separate antenna section therein.

DETAILED DESCRIPTION

Figure 1:
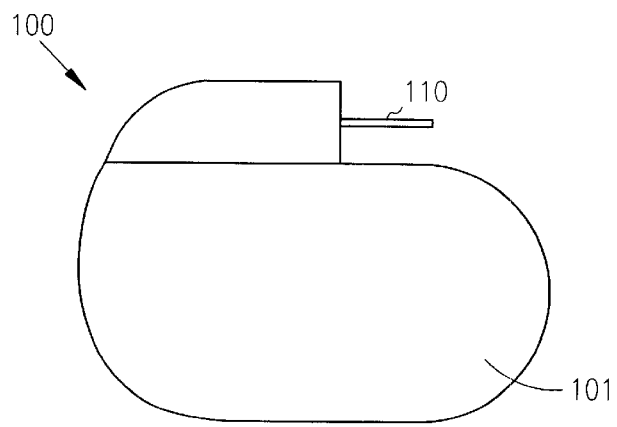
FIG. 1 shows an implantable medical device with an antenna extending from the device.

As noted above, conventional radio-frequency (RF) telemetry systems used for implantable medical devices such as cardiac pacemakers utilize inductive coupling between the antennas of the implantable device and an external programmer in order to transmit and receive RF signals. Because the induction field produced by a transmitting antenna falls off rapidly with distance, such systems require close proximity between the implantable device and a wand antenna of the external programmer in order to work properly, usually on the order of a few inches. The present invention, on the other hand, is an apparatus and method for enabling telemetry with an implantable medical device utilizing far-field radiation. Communication using far-field radiation can take place over much greater distances which makes it more convenient to use an external programmer. Also, the increased communication range makes possible other applications of the telemetry system such as remote monitoring of patients and communication with other types of external devices.

A time-varying electrical current flowing in an antenna produces a corresponding electromagnetic field configuration that propagates through space in the form of electromagnetic waves. The total field configuration produced by an antenna can be decomposed into a far-field component, where the magnitudes of the electric and magnetic fields vary inversely with distance from the antenna, and a near-field component with field magnitudes varying inversely with higher powers of the distance. The field configuration in the immediate vicinity of the antenna is primarily due to the near-field component, also known as the induction field, while the field configuration at greater distances is due solely to the far-field component, also known as the radiation field. The near-field is a reactive field in which energy is stored and retrieved but results in no net energy outflow from the antenna unless a load is present in the field, coupled either inductively or capacitively to the antenna. The far-field, on the other hand, is a radiating field that carries energy away from the antenna regardless of the presence of a load in the field. This energy loss appears to a circuit driving the antenna as a resistive impedance which is known as the radiation resistance. If the frequency of the RF energy used to drive an antenna is such that the wavelength of electromagnetic waves propagating therein is much greater than the length of the antenna, a negligible far-field component is produced. In order for a substantial portion of the energy delivered to the antenna to be emitted as far-field radiation, the wavelength of the driving signal should not be very much larger than the length of the antenna.

An antenna most efficiently radiates energy if the length of the antenna is an integral number of half-wavelengths of the driving signal. A dipole antenna, for example, is a center-driven conductor which has a length equal to half the wavelength of the driving signal. A shorter antenna can produce a similar field configuration by utilizing a ground plane to reflect electromagnetic waves emitted by the antenna and thereby produce an image field. A monopole antenna is a conductor with a length equal to one-quarter the wavelength of the driving signal situated with respect to a reflecting ground plane so that the total emitted and reflected field configuration resembles that of the dipole antenna. As will be discussed below, an antenna tuning circuit may be used to alter the effective electrical length of an antenna by loading it with capacitance or inductance.

FIG. 1 shows an exemplary implantable medical device 100 with an antenna 110 suitable for radiating and receiving far-field electromagnetic radiation extending from the device housing 101. The device housing 101 contains electronic circuitry for providing particular functionality to the device such as cardiac rhythm management, physiological monitoring, drug delivery, or neuromuscular stimulation as well as providing RF communications. The antenna 110 includes a conductor covered by insulation that is electrically connected to a radio-frequency transmitter/receiver within the housing. In various embodiments, the antenna 110 may be any conductive structure capable of efficiently radiating electromagnetic energy well-known to those of skill in the art such as a rod, a wire, a patch, or a loop. The RF circuitry transmits and receives a carrier signal at a specified frequency that is modulated with telemetry data.

In order for a substantial portion of the RF energy delivered to the antenna 110 to be emitted as far-field radiation, the length of the antenna should not be very much shorter than one-quarter of the wavelength of the RF carrier signal provided by the RF transmitter. In an exemplary embodiment, the carrier signal is selected to be 1 gigahertz which corresponds to a wavelength of approximately 32 cm. A quarter-wavelength monopole antenna can be formed by a wire antenna having a length approximately 8 cm with the housing 101 being made of metal and serving as a ground plane. The device 100 can then be implanted in an appropriate body location with the antenna 110 extending from the device housing.

In another embodiment of the invention, an antenna may be incorporated into a therapy lead of a cardiac rhythm management device. Such leads are designed to be disposed intravascularly and serve to connect rhythm control circuitry within the device housing to electrodes that deliver stimulation and sense cardiac activity in the heart. Cardiac rhythm management devices, which include pacemakers and implantable cardioverter/defibrillators, are battery-powered implantable devices with rhythm control circuitry for sensing cardiac activity and electrically stimulating the heart by means of one or more electrodes in electrical contact with the myocardium. Such stimulation is used either to pace the heart or to terminate arrhythmias such as ventricular fibrillation. A cardiac rhythm management device is usually implanted subcutaneously on the patient's chest, and a therapy lead threaded through the vessels of the upper venous system into the heart connects the rhythm control circuitry of the device to an electrode or electrode pair. Typically, such therapy leads are either unipolar or bipolar with one or two electrodes, respectively, at the distal end of the lead which can be used for either sensing or stimulation of the heart. The lead includes a conductor for each electrode surrounded by an insulating covering, with the conductor or conductors constituting a wire antenna in addition to electrically connecting the sensing/stimulation electrode to circuitry within the device housing. Such a therapy lead, or a similar structure, may also be used as a dedicated antenna.

Figure 2:
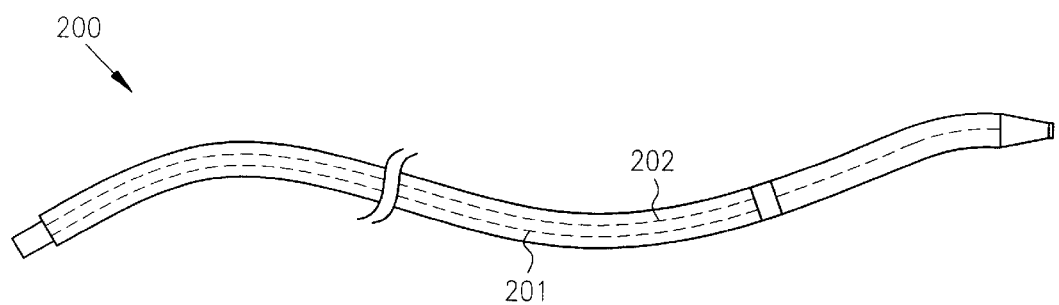
FIG. 2 shows a bipolar therapy lead.

FIG. 2 is a cross-sectional view of a bipolar therapy lead 200 showing conductors 201 and 202 that connect to a ring electrode 211 and tip electrode 212, respectively. The conductors 201 and 202 are normally used to convey stimulation pulses and sensing signals to and from the electrodes. The conductors are insulated from one another within the lead and may be coiled so as to impart flexibility to the lead. The conductors can also be driven with RF energy, however, and serve as an antenna for transmitting and receiving RF signals similar to that described above with reference to FIG. 1. Incorporating an antenna into an intravascularly disposed therapy lead allows the antenna to be longer than an antenna confined to the proximity of the housing in its implanted location and thus permits the use of lower carrier frequencies. For example, a carrier frequency of 403 megahertz corresponds to a wavelength of approximately 74 cm. A quarter-wavelength monopole antenna may then be formed by a therapy lead with an antenna of about 18 cm in length, which length can easily be accommodated within the vasculature.

Figure 3:
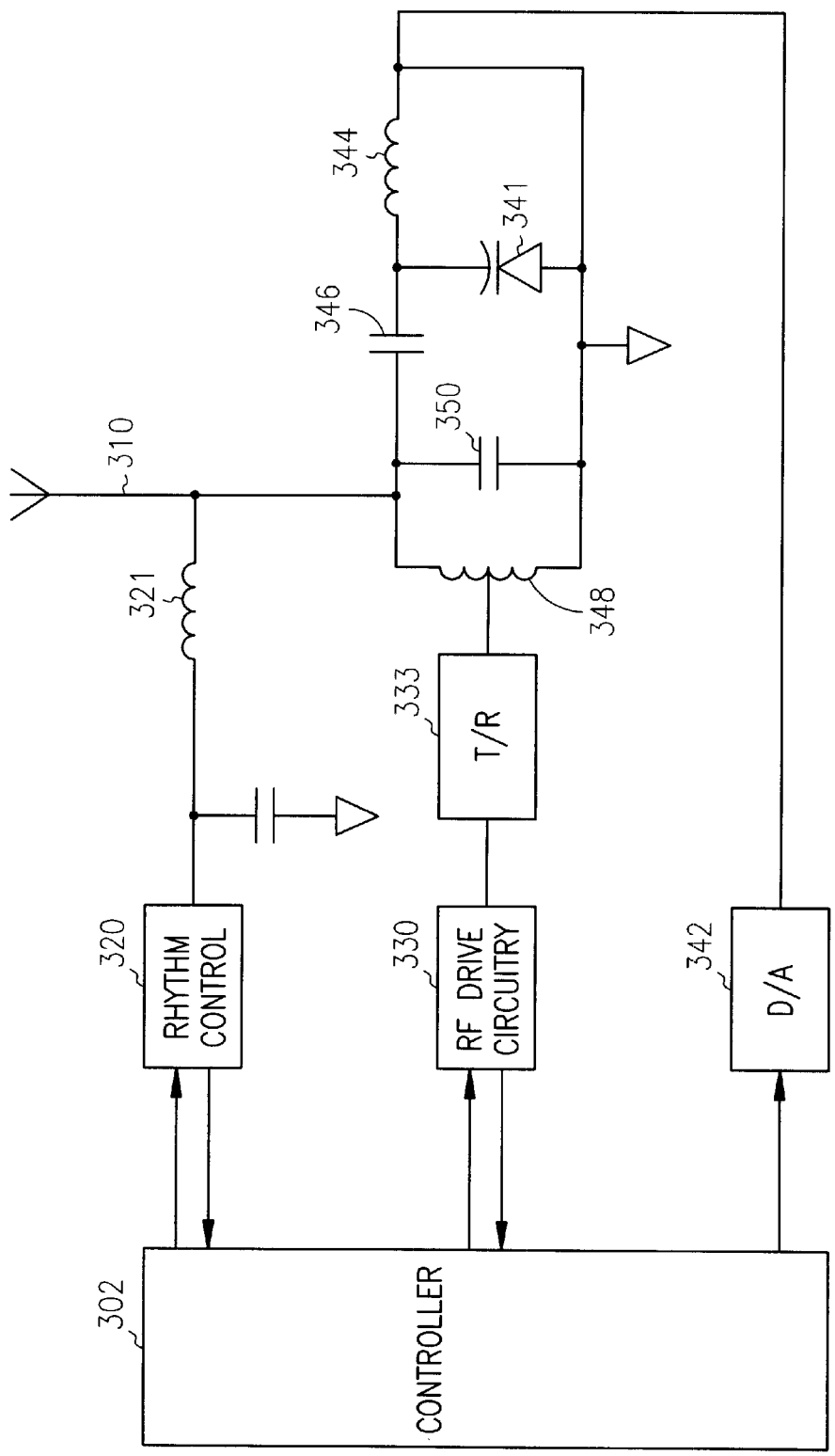
FIG. 3 is a block diagram of a cardiac rhythm management device utilizing a therapy lead as an antenna.

FIG. 3 is a block diagram of a cardiac rhythm management device in which a therapy lead 310 is used as an RF antenna. The device includes a metallic housing (shown as housing 101 in FIG. 1 and typically made of titanium) with feedthroughs for enabling the therapy leads to connect to components internal to the housing. In the figure, only one therapy lead 310 is shown but it should be understood that a cardiac rhythm management device may use two or more such leads. A microprocessor controller 302 controls the operation of the rhythm control circuitry 320. Rhythm control circuitry 320 includes sensing and stimulus generation circuitry that are connected to electrodes by the therapy leads. The conductors of the therapy lead 310 connect to rhythm control circuitry 320 through an RF choke filter 321 that serves to isolate the circuitry 320 from RF signals that are received by the antenna/lead 310 or are transmitted to the antenna by RF drive circuitry 330. The RF drive circuitry 330 includes an RF transmitter and receiver that are connected by a transmit/receive switch 333 to the antenna. The microprocessor 302 outputs and receives the data contained in the modulated carrier generated or received by the drive circuitry 330.

In this embodiment, the RF drive circuitry 330 is connected to the antenna/lead 310 through an antenna tuning circuit which loads the antenna/lead 310 with a variable amount of inductance or capacitance to thereby adjust the effective electrical length of the antenna and match the antenna impedance to the impedance of the transmitter/receiver. In this manner, the reactance of the antenna may be tuned out so that the antenna forms a resonant structure at the specified carrier frequency and efficiently transmits/receives far-field radiation. The tuning circuit in this embodiment is a tank circuit made up of an inductor 348 and a capacitor 350. A variable amount of capacitance is added to the tank circuit by a varactor diode 341 that can be controlled by a tuning bias voltage provided by a digital-to-analog converter 342. An RF choke filter 344 isolates the digital-to-analog converter 342 from the RF circuitry while allowing it to set the DC voltage of the varactor diode 341.

A DC blocking capacitor 346 isolates the RF circuitry from the DC voltage across the varactor diode. By adjusting the voltage of the varactor diode 341, the antenna can be tuned to various carrier frequencies under control of the microprocessor. This makes it possible to use various antenna structures of different dimensions at a specified carrier frequency as well as to efficiently radiate energy at a wide range of frequencies. Examples of antenna structures with which the tuning circuit can be used include antennas disposed within a non-conductive portion of the housing and patch antennas mounted on the housing, as well as lead or other antennas extending from the housing as described herein.

When a therapy lead is used as an antenna as described above, RF energy may also be delivered to the heart through the electrodes of the lead when the antenna is transmitting. This energy is minimal, however, since at 403 MHz and at 25 microwatts of transmitted power, the voltage induced on an electrode of a therapy lead will only be about 1 or 2 millivolts during transmission. (When the antenna is receiving an RF signal at that power level and frequency, the induced voltage on the electrode will be much less, on the order of a few microvolts.) This is well below the pacing threshold and should not interfere with the intrinsic activity of the heart. Also, the frequency of the RF signal is such that the duration of voltage pulses at the lead electrode is too short to stimulate the heart. To further ensure that an arrhythmia will not be induced by an RF transmission, however, telemetry bursts from the implanted device can be made synchronous with detected intrinsic activity or with pacing pulses.

Figure 4:
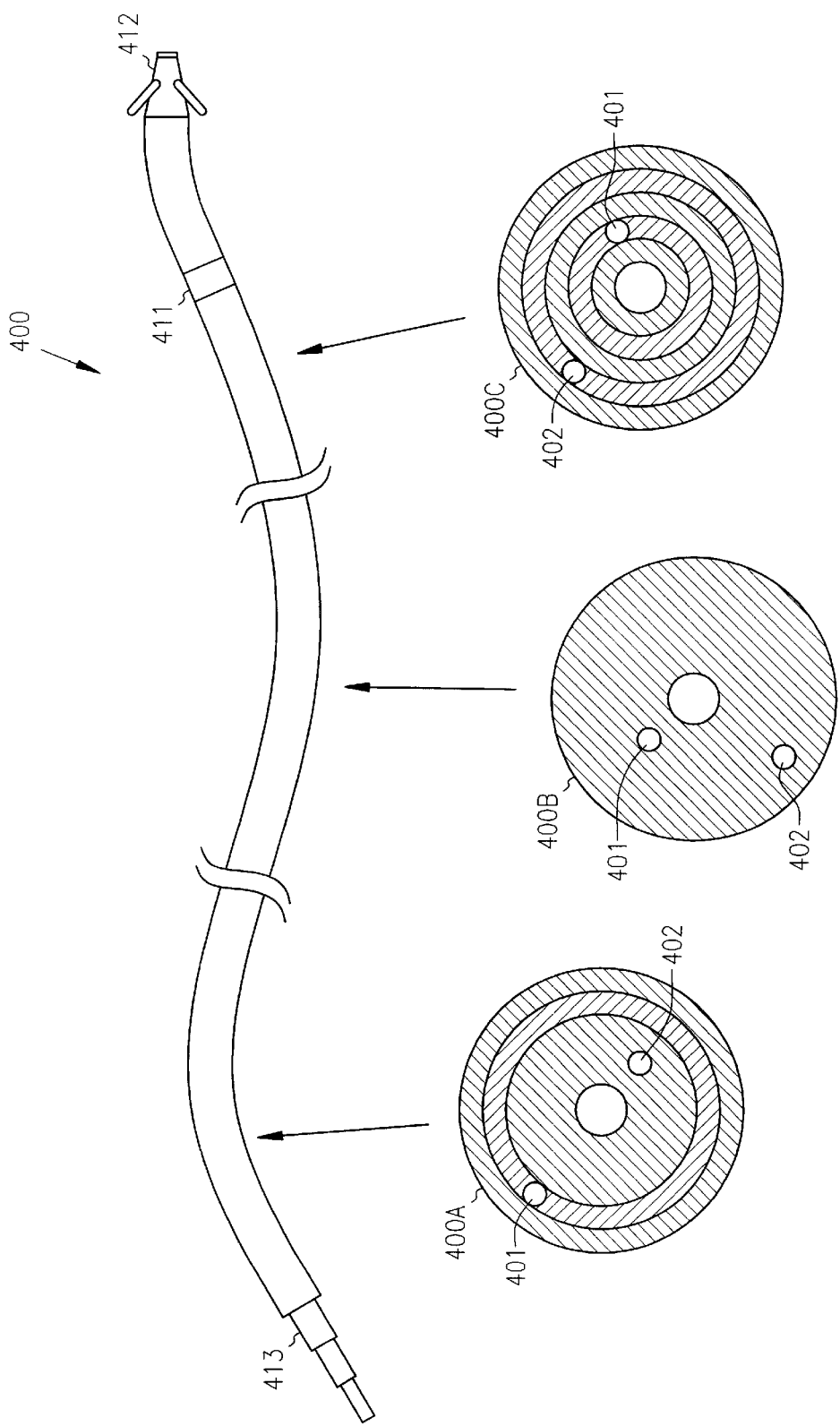
FIG. 4 shows a therapy lead with a separate antenna section.

Although standard therapy leads in use today can be used as a far-field antenna as described above, a therapy lead can also be designed with specific features for antenna use. FIG. 4 shows such a therapy lead 400 in longitudinal cross-section. A transverse cross-sectional view of three separate sections of the lead, designated 400a through 400c, is also shown. The lead is a bipolar lead with conductors 401 and 402 connected to ring and tip electrodes 411 and 412, respectively, located at the distal end of the lead. At the proximal end of the lead is a connector assembly 413 for connecting to the cardiac rhythm management device. The conductors within the lead constitute a transmission line, the characteristics of which are determined by their geometrical arrangement. For example, helically coiling the conductor increases the inductance of the line and decreasing the distance between the conductors increases the capacitance. In a distal section 400c of the lead shown in FIG. 4, the conductors 401 and 402 may be disposed close together to result in enough parasitic capacitance between the tip and ring electrodes to form a low-pass filter that effectively removes any RF frequencies from the signal transmitted to or from the electrodes. Inductance can also be added to section by coiling the conductors to form resonant trap or notch filter that removes a specified RF frequency band. In the middle section 400b of the lead, the conductors 401 and 402 are arranged in parallel and at a sufficient distance apart to radiate electromagnetic energy and thereby form a radiating section. The radiating section of the lead can be made to be one-quarter wavelength of the RF carrier frequency and used with a ground plane to efficiently produce far-field radiation. In order to facilitate the placement of the lead in the body without affecting the desired one-quarter wavelength of the radiating section, a proximal section 400a is provided in which the conductors are geometrically arranged so as to be relatively non-radiating. In a particular embodiment, one of the conductors 401 or 402 is helically wound around the other so as to serve as shielding similar to a coaxial cable with line currents confined to the inner surface of the outer conductor. The section 400a thus constitutes a transmission-line section that conveys RF energy to the radiating section 400b without affecting the field configuration. This allows the section 400a to be coiled or otherwise arranged by the physician during lead implantation without affecting the radiating part of the antenna.

Although the invention has been described in conjunction with the foregoing specific embodiment, many alternatives, variations, and modifications will be apparent to those of ordinary skill in the art. Such alternatives, variations, and modifications are intended to fall within the scope of the following appended claims.

What is claimed is:

1. An implantable medical device, comprising:
    a housing for containing electronic circuitry;
    an antenna extending from the housing;
    circuitry within the housing for transmitting or receiving a modulated radio-frequency carrier at a specified frequency to or from the antenna; and,
    wherein the electrical length of the antenna is approximately one-quarter wavelength or greater of the radio-frequency carrier at the specified frequency.

2. The device of claim 1 further comprising an antenna tuning circuit for adjusting the electrical length of the antenna by loading the antenna with inductance or capacitance.

3. The device of claim 1 wherein the housing serves as a ground plane for the antenna.

4. The device of claim 1 wherein the device is a cardiac rhythm management device having rhythm control circuitry electrically connected by one or more conductors within a therapy lead to an electrode adapted for disposition within the heart, and further wherein the antenna is formed by the conductors of the therapy lead.

5. The device of claim 4 further comprising a choke filter for blocking radio-frequency signals from the rhythm control circuitry.

6. The device of claim 4 wherein the conductors within a proximal portion of the therapy lead are arranged so as to form a non-radiating transmission line section of the lead that can be coiled without affecting a radiating antenna section of the lead.

7. The device of claim 6 wherein one of the conductors within the proximal portion of the therapy lead is helically wound around the other conductor.

8. The device of claim 4 wherein the conductors within a distal portion of the lead adjacent to the electrode are arranged to form a filter section that blocks the transmission of radio-frequency energy to or from the electrode.

9. The device of claim 4 wherein the conductors within a distal portion of the lead adjacent to the electrode are arranged to form a notch filter section that blocks the transmission of radio-frequency energy at a specified frequency band to or from the electrode.

10. A method for transmitting and receiving radio-frequency signals in an implantable medical device, comprising:
    transmitting or receiving a modulated radio-frequency carrier at a specified frequency to or from an antenna extending from a housing for the device; and,
    transmitting the radio-frequency signal at a wavelength that is approximately four times or less the electrical length of the antenna.

11. The method of claim 10 further comprising adjusting the electrical length of the antenna by loading the antenna with inductance or capacitance using a tuning circuit.

12. The method of claim 10 further comprising transmitting the radio-frequency signal at a wavelength that corresponds to a resonant frequency of the antenna.

13. The method of claim 10 further comprising employing the housing as a ground plane for the antenna.

14. The method of claim 10 further comprising transmitting the radio-frequency signal at a wavelength that is approximately four times the electrical length of the antenna.

15. The method of claim 10 wherein the antenna is incorporated within a therapy lead of a cardiac rhythm management device.

16. An implantable medical device, comprising:
   a housing for containing electronic circuitry;
   an antenna dimensioned such that a significant portion of radio-frequency energy delivered to it at a specified frequency is emitted as far-field radiation;
   circuitry within the housing for transmitting or receiving a modulated radio-frequency carrier at the specified frequency to or from the antenna; and,
   a tuning circuit for matching the impedance of the antenna to a transmitter or receiver and altering the effective electrical length of the antenna.

17. The device of claim 16 wherein the tuning circuit comprises a tank circuit connected to a varactor diode that adds a variable amount of capacitance to the tank circuit.

18. The device of claim 16 wherein the tuning circuit further comprises a digital-to-analog converter for providing a tuning bias voltage to the varactor diode so that the antenna can be selectively tuned to various carrier frequencies with a digital output.

19. The device of claim 16 further comprising a blocking capacitor for isolating the tank circuit and antenna from a DC voltage applied across the varactor diode.

20. The device of claim 17 further comprising a choke filter for isolating the digital-to-analog converter from radio-frequency energy.

21. The device of claim 16 wherein the housing serves as a ground plane for the antenna.

22. The device of claim 16 wherein the device is a cardiac rhythm management device having rhythm control circuitry electrically connected by one or more conductors within a therapy lead to an electrode adapted for disposition within the heart, and further wherein the antenna is formed by the conductors of the therapy lead.

23. The device of claim 22 wherein the conductors within a proximal portion of the therapy lead are arranged so as to form a non-radiating transmission line section of the lead that can be coiled without affecting a radiating antenna section of the lead.

24. The device of claim 23 wherein one of the conductors within the proximal portion of the therapy lead is helically wound around the other conductor.

25. The device of claim 22 wherein the conductors within a distal portion of the lead adjacent to the electrode are arranged to form a filter section that blocks the transmission of radio-frequency energy to or from the electrode.

26. The device of claim 22 wherein the conductors within a distal portion of the lead adjacent to the electrode are arranged to form a notch filter section that blocks the transmission of radio-frequency energy at a specified frequency band to or from the electrode.

27. An implantable cardiac rhythm management device, comprising:
   a housing for containing electronic circuitry;
   rhythm control circuitry electrically connected by one or more conductors within a therapy lead to an electrode adapted for disposition within the heart
   an antenna extending from the housing, wherein the antenna is formed the conductors of the therapy lead;
   wherein the conductors within a proximal portion of the therapy lead are arranged so as to form a non-radiating transmission line section of the lead that can be coiled without affecting a radiating antenna section of the lead; and,
   circuitry within the housing for transmitting or receiving a modulated radio-frequency carrier at a specified frequency to or from the antenna.

28. The device of claim 27 wherein one of the conductors within the proximal portion of the therapy lead is helically wound around the other conductor.

29. An implantable cardiac rhythm management device, comprising:
   a housing for containing electronic circuitry;
   rhythm control circuitry electrically connected by one or more conductors within a therapy lead to an electrode adapted for disposition within the heart
   an antenna extending from the housing, wherein the antenna is formed the conductors of the therapy lead;
   wherein the conductors within a distal portion of the lead adjacent to the electrode are arranged to form a filter section that blocks the transmission of radio-frequency energy to or from the electrode; and,
   circuitry within the housing for transmitting or receiving a modulated radio-frequency carrier at a specified frequency to or from the antenna.

30. An implantable cardiac rhythm management device, comprising:
   a housing for containing electronic circuitry;
   rhythm control circuitry electrically connected by one or more conductors within a therapy lead to an electrode adapted for disposition within the heart
   an antenna extending from the housing, wherein the antenna is formed the conductors of the therapy lead;
   wherein the conductors within a distal portion of the lead adjacent to the electrode are arranged to form a notch filter section that blocks the transmission of radio-frequency energy at a specified frequency band to or from the electrode; and,
   circuitry within the housing for transmitting or receiving a modulated radio-frequency carrier at a specified frequency to or from the antenna.

* * * * *